US00PP16042P2

(12) United States Plant Patent
Kolster

(10) Patent No.: US PP16,042 P2
(45) Date of Patent: Oct. 18, 2005

(54) ROSE PLANT NAMED 'KOLGIAN'

(50) Latin Name: *Rosa hybrida*
Varietal Denomination: Kolgian

(75) Inventor: Peter Rudolf Kolster, Boskoop (NL)

(73) Assignee: Gebr. Kolster B.V., Boskoop (NL)

( * ) Notice: Subject to any disclaimer, the term of this patent is extended or adjusted under 35 U.S.C. 154(b) by 41 days.

(21) Appl. No.: 10/878,423

(22) Filed: Jun. 28, 2004

(51) Int. Cl.[7] ..... A01H 5/00

(52) U.S. Cl. ..... Plt./107

(58) Field of Search ..... Plt./101, 102, 107, Plt./148

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of Rose plant named 'Kolgian', characterized by its upright and outwardly spreading plant habit; dark green-colored leaflets; sparse thorns; single pink-colored flowers; large glossy red-colored fruits; and good postproduction longevity.

2 Drawing Sheets

Botanical classification/cultivar designation: *Rosa hybrida* cultivar Kolgian.

BACKGROUND OF THE INVENTION

The present Invention relates to a new and distinct cultivar of Rose plant, botanically known as *Rosa hybrida*, commercially used as cut stems with fruits or hips, and hereinafter referred to by the name 'Kolgian'.

The new Rose is a product of a planned breeding program conducted by the Inventor in Boskoop, The Netherlands. The objective of the breeding program was to develop cut Rose varieties with large and attractive-colored fruits.

The new cultivar originated from a cross-pollination made by the Inventor in 1997 of two unidentified proprietary seedling selections, not patented. The cultivar Kolgian was discovered and selected by the Inventor in 1999 as a single flowering plant within the progeny of the stated cross-pollination in a controlled environment in Boskoop, The Netherlands.

Asexual reproduction of the new Rose by terminal cuttings at Boskoop, The Netherlands since 2000, has shown that the unique features of this new Rose are stable and reproduced true to type in successive generations of asexual reproduction.

SUMMARY OF THE INVENTION

The following traits have been repeatedly observed and are determined to be the unique characteristics of 'Kolgian'. These characteristics in combination distinguish 'Kolgian' as a new and distinct cultivar:

1. Upright and outwardly spreading plant habit.
2. Dark green-colored leaflets.
3. Sparse thorns.
4. Single pink-colored flowers.
5. Large glossy red-colored fruits.
6. Good postproduction longevity.

Plants of the new Rose differ from plants of the parent seedling selections primarily in flower and fruit coloration.

Plants of the new Rose can be compared to plants of the Rose cultivar Kolsens, not patented. In side-by-side comparisons conducted in Boskoop, The Netherlands, plants of the new Rose differed from plants of the cultivar Kolsens primarily in fruit size as plants of the new Rose produced larger hips than plants of the cultivar Kolsens.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph at the top of the first sheet comprises a side perspective view of a typical plant of 'Kolgian'.

The photograph at the bottom of the first sheet is a close-up view of the upper surface of a typical fully expanded leaf of 'Kolgian'.

The photograph at the top of the second sheet is a close-up view of typical flowers of 'Kolgian'.

The photograph at the bottom of the second sheet is a close-up view of typical fruits of 'Kolgian'.

DETAILED BOTANICAL DESCRIPTION

The new Rose has not been observed under all possible environmental conditions. The phenotype may vary somewhat with variations in environment such as temperature and light intensity, without, however, any variance in genotype.

The aforementioned photographs, following observations and measurements describe plants grown in Boskoop, The Netherlands, in an outdoor nursery and under commercial production practices. Plants were about three years old. The photographs and description were taken during the late summer when outdoor day temperatures ranged from 14 to 30° C. and night temperatures ranged from 7 to 14° C. In the following description, color references are made to The Royal Horticultural Society Colour Chart, 2001 Edition, except where general terms of ordinary dictionary significance are used.

Botanical classification: *Rosa hybrida* cultivar Kolgian.

Parentage:

*Female parent.*—Unidentified proprietary selection of *Rosa hybrida*, not patented.

*Male parent.*—Unidentified proprietary selection of *Rosa hybrida*, not patented.

Propagation:

*Type.*—Terminal cuttings.

*Time to initiate roots.*—About 40 days at 12 to 16° C.

*Time to produce a rooted young plant.*—About three months at 12 to 16° C.

*Root description.*—Freely branching; medium thickness; soft brown in color.

Plant description:

*Plant form.*—Upright and outwardly spreading perennial shrub; broadly ovate in overall shape.

*Growth habit.*—Moderately vigorous. Freely branching; dense and bushy growth habit.

*Growth rate.*—During the spring in Boskoop, The Netherlands, plants grow about 20 cm per month.

*Plant height.*—About 1.25 meters.

*Plant width* (*spread*).—About 1 meter.

*Lateral branches.*—Quantity per plant: About eight. Length: About 31 cm. Diameter: About 4 mm. Internode length: About 3 cm. Strength: Strong. Texture: Smooth, glabrous. Color: 144A. Thorns: Density: Sparse. Shape: Triangular with sharp acuminate apices. Height: About 3 mm. Diameter, at base: About 5 mm. Color: 181A.

*Foliage description.*—Leaves alternate; compound with five to nine leaflets. Leaf length: About 11 cm. Leaf width: About 4.1 cm. Leaflet length: About 6.5 cm. Leaflet width: About 2.5 cm. Leaflet shape: Ovate. Leaflet apex: Acute. Leaflet base: Rounded. Leaflet margin: Serrate. Leaflet texture, upper and lower surfaces: Smooth, glabrous. Leaflet venation pattern: Pinnate. Leaflet color: Developing leaflets, upper surface: Between 137B and 143A. Developing leaflets, lower surface: Between 138A and 138B. Fully expanded leaflets, upper surface: 139A. Fully expanded leaflets, lower surface: 137B to 137C. Venation, upper surface: 143B. Venation, lower surface: 144C. Leaf petiole: Length: About 2.1 cm. Diameter: About 1.5 mm. Texture, upper and lower surfaces: Smooth, glabrous. Color, upper surface: 144C, occasionally overlain with 180A to 180B. Color, lower surface: 144C. Stipules: Quantity per leaf: Two. Arrangement: One stipule on either side of the leaf petiole. Shape: Lanceolate. Length: About 2.1 cm. Diameter: Less than 1 cm. Color, upper surface: 139A. Color, lower surface: 137B to 137C.

Flower description:

*Flower type and habit.*—Pink-colored single rotate flowers arranged in compound corymbs with about 28 flowers and flower buds per corymb. Flowers not persistent. Flowers face mostly upright or outward.

*Natural flowering season.*—Mid to late summer, typically July through September in Boskoop, The Netherlands; flowering continuous during this period.

*Postproduction longevity.*—Cut stems are typically harvested when all flowers have developed fruits. Flowers typically last a few days. Postproduction longevity of cut stems with fruits is typically more than two weeks.

*Fragrance.*—Strong, typical of *Rosa*, sweet, pleasant.

*Flower buds.*—Height: About 3.5 mm. Diameter: About 1.2 mm. Shape: Narrowly ovoid. Color: 143A to 143B; densely covered with glandular hairs, 145B to 145C; glands, 187A.

*Flowers.*—Diameter: About 6.3 cm. Depth: About 1.2 cm.

*Petals.*—Quantity per flower: Five. Length: About 3.2 cm. Width: About 3.6 cm. Shape: Obcordate, broad. Aspect: Slightly reflexed. Apex: Retuse. Base: Attenuate. Margin: Entire. Texture, upper and lower surfaces: Smooth, glabrous. Color: Developing, upper and lower surfaces: 75A to 75B; towards the base, lighter than 75B. Fully expanded, upper and lower surfaces: 75B; towards the base, lighter than 75B.

*Sepals.*—Quantity per flower: Five. Length: About 2.2 cm. Width: About 7 mm. Shape: Lanceolate. Apex: Narrowly acute, elongate. Base: Broadly cuneate. Margin: Entire. Texture: Upper surface: Smooth. Lower surface: Densely covered with glandular hairs. Color: Developing and fully expanded sepals, upper surface: 138D; towards the margins, 138A. Developing and fully expanded sepals, lower surface: 143A.

*Peduncles.*—Length: About 9 cm. Diameter: About 2 mm. Orientation: Erect to about 30° from vertical. Strength: Strong. Color: 143A to 143B.

*Pedicels.*—Length: About 2.2 cm. Diameter: About 1.2 mm. Orientation: Erect to about 40° from vertical. Strength: Strong. Color: 143A to 143B.

*Reproductive organs.*—Stamens: Quantity per flower: More than 150. Anther shape: Narrowly oblong. Anther length: About 2 mm. Anther color: 13B. Pollen amount: Abundant. Pollen color: 8A. Pistils: Quantity per flower: About 30. Pistil length: About 0.5 mm. Stigma shape: Oval, flattened. Stigma color: 153D. Style length: Less than 0.5 mm; minute. Ovary color: 143A to 143B.

*Fruits.*—Quantity per flower: One. Days to ripening: About 40. Type: Fleshy hip. Shape: Roughly oblate. Length: About 1.5 cm. Diameter: About 2 cm. Texture: Smooth, glabrous. Color: 42A; towards the base, 33A to N34B; glossy.

*Seeds.*—Quantity per fruit: About 15. Length: About 4 mm. Diameter: About 3 mm. Color: 163C.

Disease susceptibility: Plants of the new Rose have been observed to not be susceptible to pathogens common to Rose, such as mildew and Black Spot.

Temperature tolerance: Plants of the new Rose have been observed to tolerate temperatures ranging from −30 to 35° C.

It is claimed:

1. A new and distinct cultivar of Rose plant named 'Kolgian', as illustrated and described.

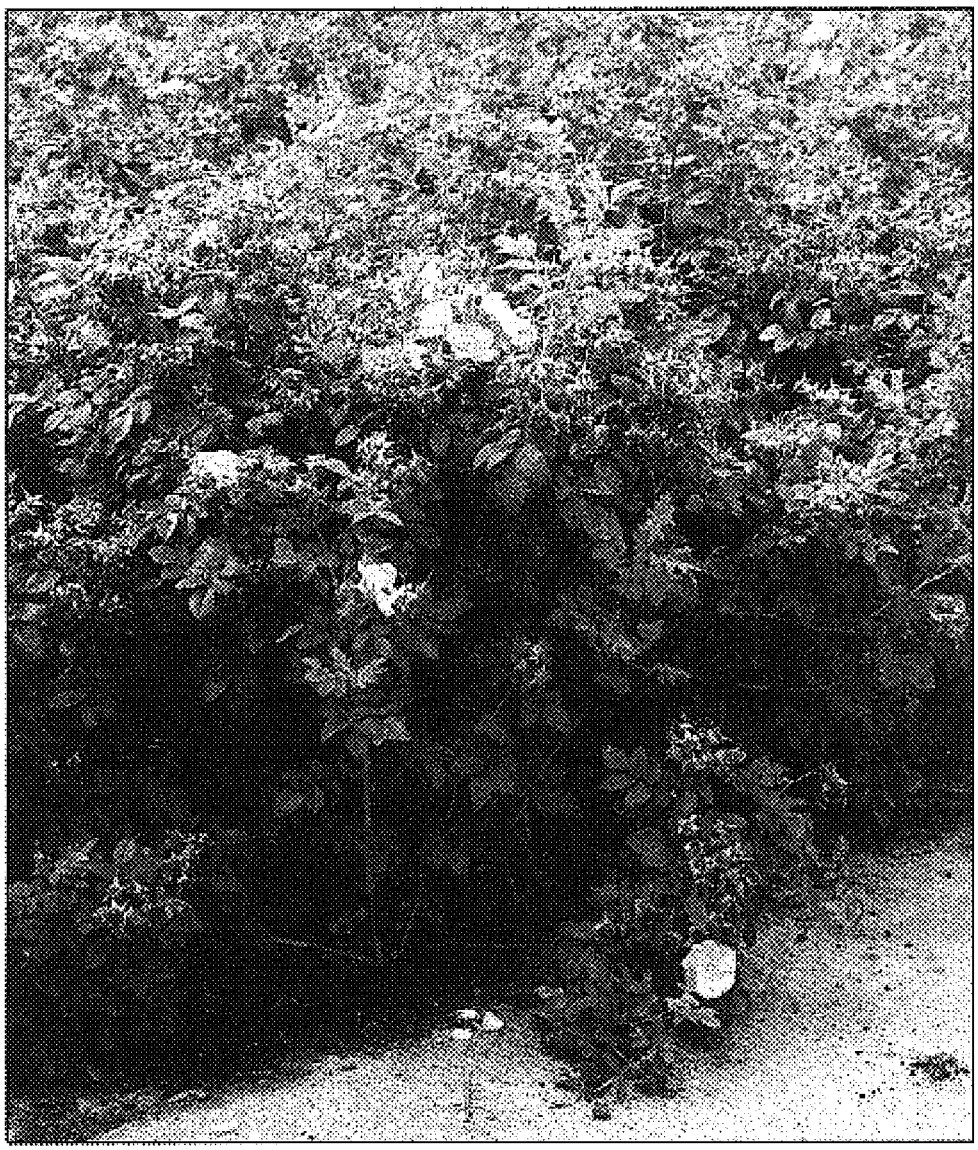
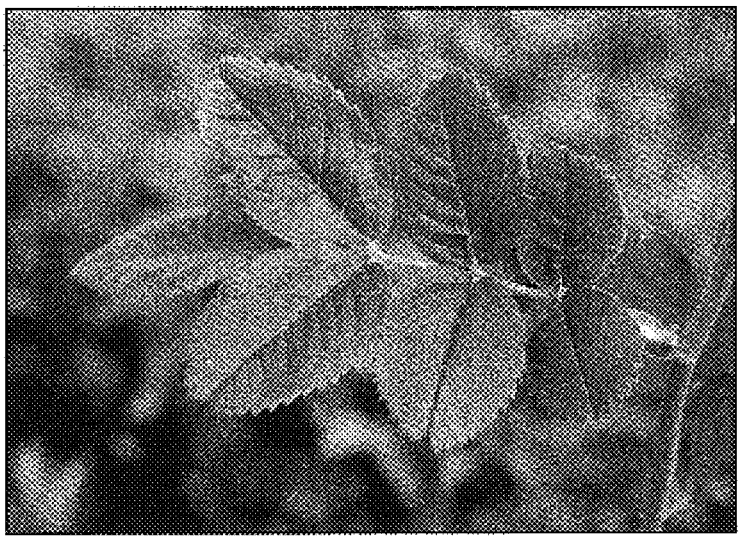

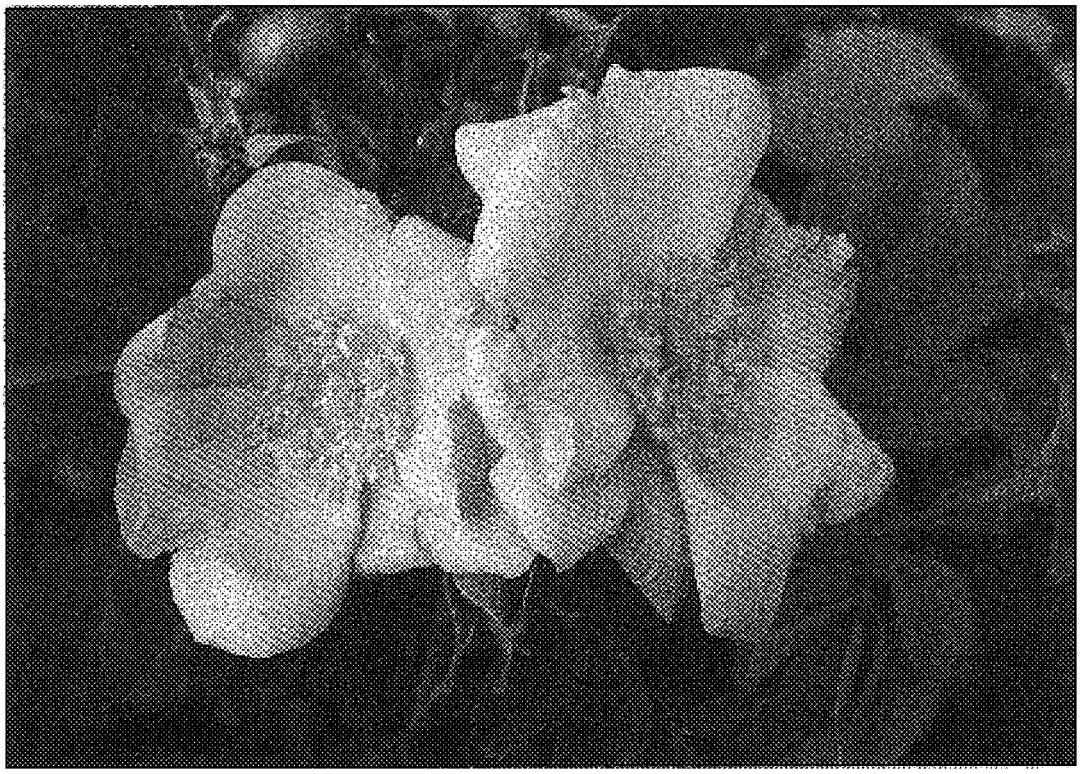
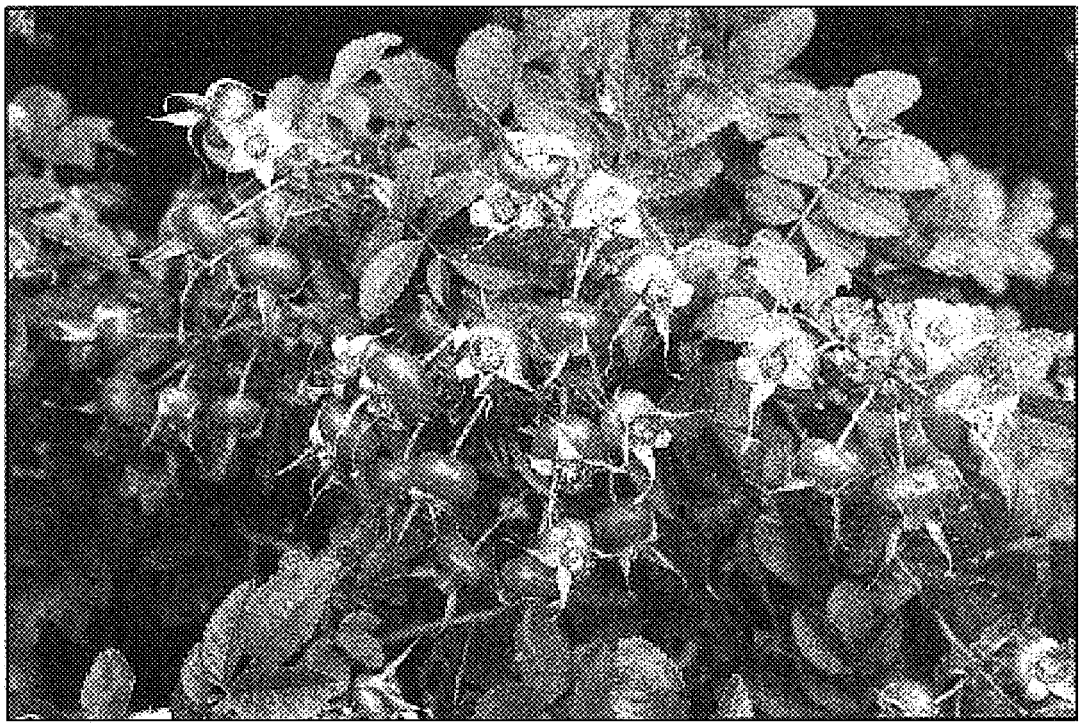

* * * * *